US011291394B2

(12) United States Patent
Lee et al.

(10) Patent No.: US 11,291,394 B2
(45) Date of Patent: Apr. 5, 2022

(54) SYSTEM AND METHOD FOR PREDICTING LUCIDITY LEVEL

(71) Applicant: KONINKLIJKE PHILIPS N.V., Eindhoven (NL)

(72) Inventors: Matthew Len Lee, New York, NY (US); Portia E. Singh, Everett, MA (US); Mladen Milosevic, Stoneham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 683 days.

(21) Appl. No.: 15/759,544

(22) PCT Filed: Aug. 31, 2016

(86) PCT No.: PCT/IB2016/055187
§ 371 (c)(1),
(2) Date: Mar. 13, 2018

(87) PCT Pub. No.: WO2017/046669
PCT Pub. Date: Mar. 23, 2017

(65) Prior Publication Data
US 2019/0150820 A1    May 23, 2019

Related U.S. Application Data

(60) Provisional application No. 62/218,130, filed on Sep. 14, 2015.

(51) Int. Cl.
*A61B 5/316*    (2021.01)
*A61B 5/16*    (2006.01)
(Continued)

(52) U.S. Cl.
CPC .......... *A61B 5/165* (2013.01); *A61B 5/0205* (2013.01); *A61B 5/1118* (2013.01);
(Continued)

(58) Field of Classification Search
CPC .............................. A61B 5/165; A61B 5/1118
See application file for complete search history.

(56) References Cited

U.S. PATENT DOCUMENTS

| 7,006,872 B2 | 2/2006 | Gielen et al. |
| 2001/0021800 A1* | 9/2001 | Balkin ................ A61B 5/16 600/300 |

(Continued)

FOREIGN PATENT DOCUMENTS

| WO | 2005079332 A2 | 9/2005 |
| WO | 2013162698 A1 | 10/2013 |

OTHER PUBLICATIONS

Burns, et al., "Harnessing Context Sensing to Develop a Mobile Intervention for Depression", Journal o f Medical Internet Research 2011, vol. 13, Issue 3, pp. 1-17.

*Primary Examiner* — Michael J D'Abreu (57) ABSTRACT

The present disclosure pertains to a system configured to predict a lucidity level of a subject. The system comprises one or more activity sensors configured to generate output signals conveying information related to physical activity of the subject; one or more physiological sensors configured to generate output signals conveying information related to physiological parameters of the subject; a user interface configured to receive information related to a mood of the subject and information related to a cognitive state of the subject; and one or more processors configured to: generate an electronic lucidity model for the subject based on previous physical activity information, previous physiological parameter information, previous mood information, and previous cognitive state information; and predict the lucidity level of the subject based on the electronic lucidity model and one or more of current physical activity information, current physiological parameter information, current mood information, or current cognitive state information.

18 Claims, 3 Drawing Sheets

(51) Int. Cl.
*A61B 5/11* (2006.01)
*G16H 10/60* (2018.01)
*G16H 50/20* (2018.01)
*A61B 5/0205* (2006.01)
*A61B 5/00* (2006.01)
*A61B 5/021* (2006.01)
*A61B 5/024* (2006.01)
*A61B 5/145* (2006.01)

(52) U.S. Cl.
CPC .......... *A61B 5/7267* (2013.01); *A61B 5/7275* (2013.01); *A61B 5/7475* (2013.01); *G16H 10/60* (2018.01); *G16H 50/20* (2018.01); *A61B 5/0077* (2013.01); *A61B 5/021* (2013.01); *A61B 5/024* (2013.01); *A61B 5/1112* (2013.01); *A61B 5/14532* (2013.01); *A61B 5/4806* (2013.01); *A61B 5/4875* (2013.01); *A61B 5/6898* (2013.01)

(56) References Cited

U.S. PATENT DOCUMENTS

| | | |
|---|---|---|
| 2005/0277813 A1 | 12/2005 | Katz et al. |
| 2012/0310050 A1 | 12/2012 | Osorio |
| 2013/0036080 A1 | 2/2013 | Kane-Esrig |
| 2014/0279728 A1 | 9/2014 | Skole |
| 2018/0289314 A1* | 10/2018 | Reifman .............. A61B 5/0255 |

* cited by examiner

SYSTEM AND METHOD FOR PREDICTING LUCIDITY LEVEL

This application is the U.S. National Phase application under 35 U.S.C. § 371 of International Application No. PCT/IB2016/055187, filed on Aug. 31, 2016, which claims the benefit of U.S. Provisional Application Ser. No. 62/218,130, filed Sep. 14, 2015. These applications are hereby incorporated by reference herein.

BACKGROUND

1. Field

The present disclosure pertains to a system and method for predicting a lucidity level of a subject.

2. Description of the Related Art

Typically, the behavior of people with cognitive or mental impairments is manually observed, and behavioral issues such as wandering or distraction are dealt with by the observer after the issues occur. Systems for electronically monitoring a person's daily activities are known, but these systems do not correlate daily activities to lucidity level.

SUMMARY

Accordingly, one or more aspects of the present disclosure relate to a system configured to predict a lucidity level of a subject. The system comprises one or more activity sensors, one or more physiological sensors, a user interface, one or more hardware processors, and/or other components. The one or more activity sensors are configured to generate output signals conveying information related to physical activity of the subject. The one or more physiological sensors are configured to generate output signals conveying information related to physiological parameters of the subject. The user interface is configured to receive information related to a mood of the subject and information related to a cognitive state of the subject. The one or more hardware processors are configured by machine-readable instructions to: generate an electronic lucidity model for the subject based on previous physical activity information, previous physiological parameter information, previous mood information, and previous cognitive state information; and predict the lucidity level of the subject based on the electronic lucidity model and one or more of current physical activity information, current physiological parameter information, current mood information, or current cognitive state information.

Another aspect of the present disclosure relates to a method for predicting a lucidity level of a subject with a prediction system. The system comprises one or more activity sensors, one or more physiological sensors, a user interface, and one or more hardware processors. The method comprises: generating, with the one or more activity sensors, output signals conveying information related to physical activity of the subject; generating, with the one or more physiological sensors, output signals conveying information related to physiological parameters of the subject; receiving, with the user interface, information related to a mood of the subject and information related to a cognitive state of the subject; generating, with the one or more hardware processors, an electronic lucidity model for the subject based on previous physical activity information, previous physiological parameter information, previous mood information, and previous cognitive state information; and predicting, with the one or more hardware processors, the lucidity level of the subject based on the electronic lucidity model and one or more of current physical activity information, current physiological parameter information, current mood information, or current cognitive state information.

Still another aspect of present disclosure relates to a system configured to predict a lucidity level of a subject. The system comprises means for generating output signals conveying information related to physical activity of the subject; means for generating output signals conveying information related to physiological parameters of the subject; means for receiving information related to a mood of the subject and information related to a cognitive state of the subject; means for generating an electronic lucidity model for the subject based on previous physical activity information, previous physiological parameter information, previous mood information, and previous cognitive state information; and means for predicting the lucidity level of the subject based on the electronic lucidity model and one or more of current physical activity information, current physiological parameter information, current mood information, or current cognitive state information.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
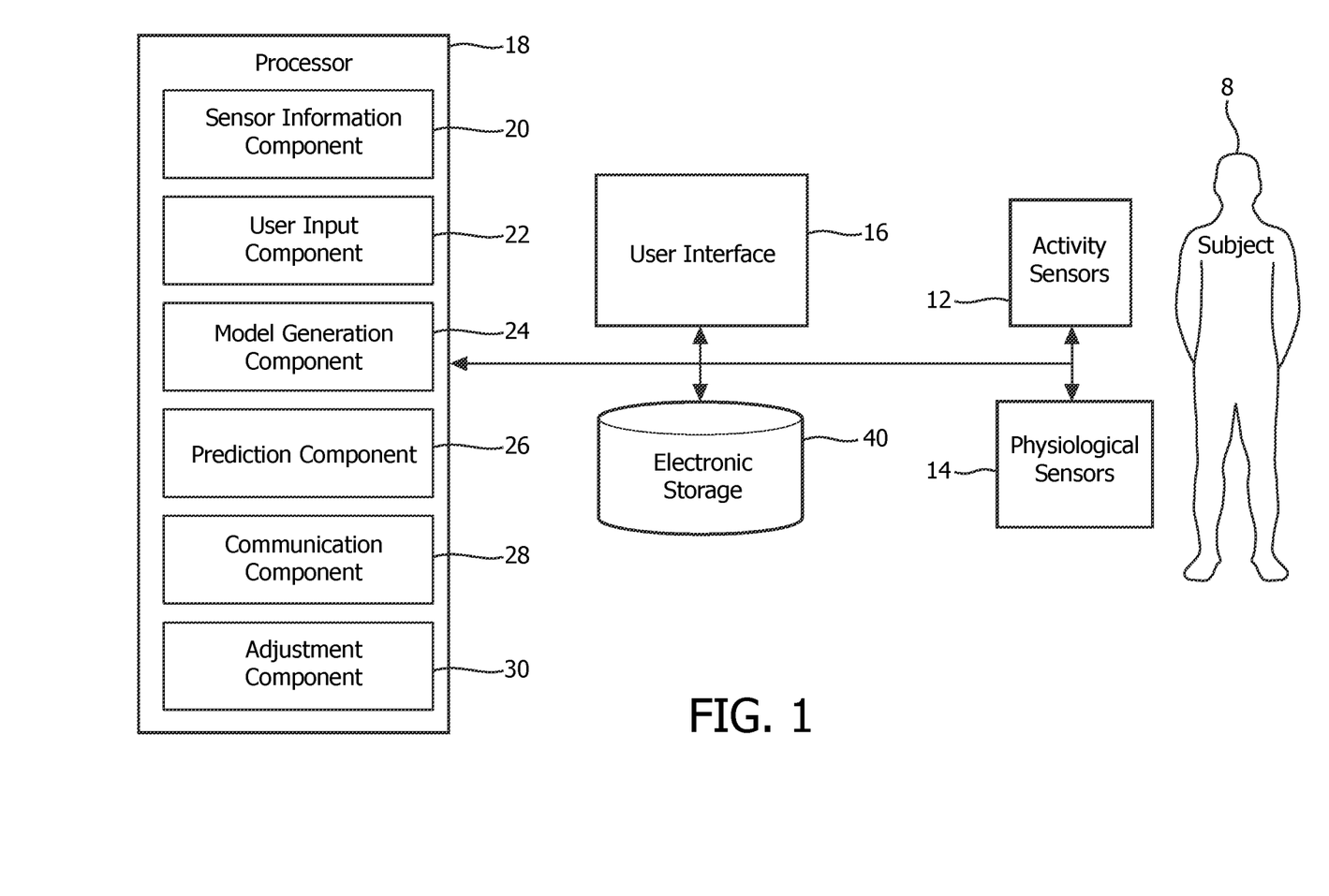
FIG. 1 is a schematic illustration of a system configured to predict a lucidity level of a subject.

FIG. 1 is a schematic illustration of a system 10 configured to determine and/or predict a lucidity level of a subject 8. In some embodiments, system 10 is configured to determine and/or predict the lucidity (and/or confusion) level of an individual (e.g., subject 8) who has cognitive impairments, and/or other individuals. System 10 detects activity information, physiological information, and/or other information about subject 8; receives information related to a mood, a cognitive state, and/or other information about subject 8 from subject 8, a caregiver, and/or other individuals; and determines and/or predicts how lucid and/or confused subject 8 is currently and/or will be in the future.

For example, system 10 may detect and/or record, in real-time and/or at other times, activities performed by subject 8 (performance of activities of daily living, interacting with others, physical activity, sleep duration/quality, etc.), physiological health information, and/or other information. System 10 may receive information about a mood of subject 8 at a given time, a cognitive state of subject 8 at a given time, and/or other information from a caregiver and/or other individuals. System 10 may generate an individualized electronic lucidity model (e.g., using machine learning as described below and/or other techniques) for subject 8 based on the detected and/or received activity, health, mood, and/or cognitive information; and output an indication of a current lucidity level of subject 8 and/or a prediction of the level of lucidity in the future (e.g., the next day). System 10 may facilitate presentation of the output lucidity information to a caregiver, receive information about the actual future lucidity of subject 8, and adjust the electronic lucidity model based on the predicted lucidity level and a future lucidity/cognitive state of subject 8 (e.g., reported by the caregiver) during a period of time that corresponds to the predicted lucidity level. System 10 learns and adjusts the electronic lucidity model over time based on predictors and/or triggers for low lucidity identified in the detected and/or received activity, health, mood, and/or cognitive information for subject 8.

Existing technologies for individuals with cognitive and/or mental impairments are typically designed to react after-the-fact to behavioral issues of an individual such as wandering and/or distraction. Some of these existing technologies cause the individual to feel stigmatized and/or restrict the autonomy of the individual who may have dynamically changing functional abilities and needs from one day to the next (e.g., people with dementia have both good days when they are lucid and can perform many activities important for their independence and also bad days when they feel confused, physically tired, and experience functional limitations). Caregivers of people with dementia (for example) commonly report that the person with dementia may be particularly confused one day and particularly lucid on another. Knowing how lucid an individual will be in the future may allow caregivers (and/or even the individual himself) to make the adjustments in the environment and/or marshal additional support for the individual with dementia. For example, on good (lucid) days an individual with dementia can generally be left alone at home safely during normal working hours while an adult child goes to work. On bad days (when the individual has low lucidity/greater confusion), the individual might need supervision during the day to make sure he does not endanger himself and that he follows routines for maintaining health (like taking medications, eating meals, etc.). A caregiver typically cannot simply stay home from work and/or request a home health aide at the last minute to care for the individual with dementia for the entire workday. Ideally, having some prediction of the lucidity of the individual may help in planning. System 10 is configured to predict functional abilities and/or needs of individuals (e.g., subject 8) with cognitive or mental impairments, and/or other individuals. System 10 is configured to provide an indication and/or prediction of when an individual is having and/or will have lucid and/or confused moments based on the detected and/or received activity, health, mood, and/or cognitive information for subject 8 from current and/or previous days, and/or other information.

In some embodiments, system 10 comprises one or more of an activity sensor 12, a physiological sensor 14, a user interface 16, a processor 18, electronic storage 40, and/or other components.

Activity sensors 12 are configured to generate output signals conveying information related to physical activity of subject 8 and/or other information. Information related to physical activity of subject 8 may include information related to physical movement and/or lack of movement (e.g., during sleep) of subject 8; performance and/or non-performance of daily activities (e.g., toileting, sleeping, eating, dressing, grooming, taking medications) by subject 8; activity duration, quantity and/or duration of interactions (social or otherwise) with other people; time duration between individual activities; an order of activities performed by subject 8; time spent in unfamiliar situations; locations visited within and/or external to the home by subject 8; the amount and quality of light that subject 8 was exposed to; an amount of time spent watching television, on the internet, or using computing devices; a type of information viewed while watching television, on the internet, or using computing devices; and/or other information.

Activity sensors 12 may comprise one or more sensors that measure such parameters directly. For example, sensors 12 may include a geolocation sensor included in a smartphone carried by subject that detects movement of subject 8. Sensors 12 may comprise one or more sensors that generate output signals conveying information related to physical activity of subject 12 indirectly. For example, one or more sensors 12 may be included in various household appliances and generate an output signal as an individual appliance is used by subject 8. The output signals of sensors 12 in the individual appliances may generate information related to the physical activities of subject 8 as subject 8 moves through the house using the individual appliances. In some embodiments, activity sensors 12 may be and/or include one or more of a motion sensor, a geolocation sensor, a proximity sensor, a sleep sensor, a clock, instrumented household appliances, a home motion sensor, a pressure sensor, a light sensor, a camera, a microphone, a wearable activity tracker, a network-connected object that senses an individual interacting with it, a smartphone, and/or other sensors.

Although sensors 12 are illustrated at a single location near subject 8, this is not intended to be limiting. Sensors 12 may include sensors disposed in a plurality of locations, such as for example, within and/or in communication with other components of system 10 (e.g., physiological sensors 14, user interface 16, processor 18), coupled (in a removable manner) with clothing of subject 8, coupled in a permanent manner with clothing of subject 8 (e.g., clothing that has permanent (passive) sensors woven into the fabric of the clothing), worn by subject 8 (e.g., as a headband, wristband, etc.), positioned to point at subject 8 (e.g., a camera that conveys output signals related to movement of subject 12), disposed in and/or formed by household appliances (e.g., smart appliances that generate output signals indicating use), and/or in other locations. Sensors 12 may generate output signals continuously, at predetermined intervals, responsive to presence of and/or interaction with subject 8, and/or at other times.

Physiological sensors 14 are configured to generate output signals conveying information related to physiological parameters of subject 8 and/or other information. Physiological parameters of subject 8 may be and/or be related to a pulse/heart rate of subject 8, a blood pressure of subject 8, blood chemistry of subject 8, hydration of subject 8, a respiration rate/output of subject 8, the blood oxygen level of subject 8, the skin conductance and/or skin temperature of subject 8, the body temperature of subject 8, the joint/muscular flexibility of subject 8, the blood circulation of subject 8, the cardiac output and/or weight of subject 8, the relative health and/or sickness of subject 8, brain activity of subject 8, and/or other parameters. Sensors 14 may comprise one or more sensors that measure such parameters directly. For example, sensors 14 may be and/or include a heart rate sensor located on the chest of subject 8. Sensors 14 may comprise one or more sensors that generate output signals conveying information related to physiological parameters of subject 8 indirectly. For example, one or more sensors 14 may generate an output with physiological parameter information based on movement of subject 8 (e.g. movement detected via actigraphy signals from a bracelet on a wrist of subject 8 may indicate a higher heart rate, respiration rate, etc.). In some embodiments, physiological sensors 14 may be and/or include one or more of a heart rate monitor, a blood pressure monitor, a blood glucose monitor, a blood oxygen saturation monitor, a hydration monitor, a skin/body temperature thermometer, a joint flexibility gauge, a weight scale, electroencephalogram (EEG) electrodes configured to detect electrical activity along the scalp of subject 8 resulting from current flows within the brain of subject 8, and/or other sensors.

Although sensors 14 are illustrated at a single location near subject 8, this is not intended to be limiting. Sensors 14 may include sensors disposed in a plurality of locations, such as for example, within and/or in communication with other components of system 10 (e.g., activity sensors 12, user interface 16 and/or processor 18 that are part of a smartphone associated with subject 8), coupled (in a removable manner) with clothing of subject 8, worn by subject 8 (e.g., as a headband, wristband, etc.), positioned to point at subject 8 (e.g., a camera that conveys output signals related to heart rate of subject 12), and/or in other locations. Sensors 14 may generate output signals continuously, at predetermined intervals, responsive to presence of and/or interaction with subject 8, and/or at other times.

User interface 16 is configured to receive information related to a mood of subject 8, information related to a cognitive state of subject 8, and/or other information. User interface 16 is configured to provide an interface between system 10 and caregivers, subject 8, and/or other users through which caregivers, subject 8, and/or other users may provide information to and receive information from system 10. This enables data, cues, results, and/or instructions and any other communicable items, collectively referred to as "information," to be communicated between a user (e.g., a caregiver, subject 8, and/or other users) and processor 18, and/or other components of system 10. For example, mood information, cognitive state information and/or other information about subject 8 may be communicated from a caregiver to system 10 via user interface 16. A current lucidity level, a predicted lucidity level, a predicted lucidity level score, and/or other information may be communicated from system 10 to the caregiver via user interface 16.

Examples of interface devices suitable for inclusion in user interface 16 comprise a graphical user interface, a display, a touchscreen, a keypad, buttons, switches, a keyboard, knobs, levers, speakers, a microphone, an indicator light, an audible alarm, a printer, a haptic feedback device, and/or other interface devices. In some embodiments, user interface 16 comprises a plurality of separate interfaces. For example, user interface 16 may comprise a plurality of different interfaces associated with a plurality of computing devices associated with different caregivers. User interface 16 is configured such that the plurality of caregivers may provide information to (e.g., the mood information, cognitive state information, etc.) and receive information from (e.g., a predicted lucidity level, etc.) system 10 via the individual ones of the plurality of user interfaces. In some embodiments, user interface 16 comprises at least one interface that is provided integrally with processor 18 and/or other components of system 10.

It is to be understood that other communication techniques, either hard-wired or wireless, are also contemplated by the present disclosure as user interface 16. For example, the present disclosure contemplates that user interface 16 may be integrated with a removable storage interface provided by electronic storage 40. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 comprise, but are not limited to, an RS-232 port, RF link, an IR link, modem (telephone, cable or other). In short, any technique for communicating information with system 10 is contemplated by the present disclosure as user interface 16.

Processor 18 is configured to provide information processing capabilities in system 10. As such, processor 18 may comprise one or more of a digital processor, an analog processor, a digital circuit designed to process information, an analog circuit designed to process information, a state machine, and/or other mechanisms for electronically processing information. Although processor 18 is shown in FIG. 1 as a single entity, this is for illustrative purposes only. In some embodiments, processor 18 may comprise a plurality of processing units. These processing units may be physically located within the same device, or processor 18 may represent processing functionality of a plurality of devices operating in coordination.

As shown in FIG. 1, processor 18 is configured to execute one or more computer program components. The one or more computer program components may comprise one or more of a sensor information component 20, a user input component 22, a model generation component 24, a prediction component 26, a communication component 28, an adjustment component 30, and/or other components. Processor 18 may be configured to execute components 20, 22, 24, 26, 28, and/or 30 by software; hardware; firmware; some combination of software, hardware, and/or firmware; and/or other mechanisms for configuring processing capabilities on processor 18.

It should be appreciated that although components 20, 22, 24, 26, 28, and 30 are illustrated in FIG. 1 as being co-located within a single processing unit, in embodiments in which processor 18 comprises multiple processing units, one or more of components 20, 22, 24, 26, 28, and/or 30 may be located remotely from the other components. The description of the functionality provided by the different components 20, 22, 24, 26, 28, and/or 30 described below is for illustrative purposes, and is not intended to be limiting, as any of components 20, 22, 24, 26, 28, and/or 30 may provide more or less functionality than is described. For example, one or more of components 20, 22, 24, 26, 28, and/or 30 may be eliminated, and some or all of its functionality may be provided by other components 20, 22, 24, 26, 28, and/or 30. As another example, processor 18 may be configured to execute one or more additional components that may perform some or all of the functionality attributed below to one of components 20, 22, 24, 26, 28, and/or 30.

Sensor information component 20 is configured to receive the information in the output signals generated by activity sensors 12, physiological sensors 14, and/or other sensors. The information may be received wirelessly and/or via wires. In some embodiments, sensor information component 20 is configured to determine one or more activity parameters, physiological parameters, and/or other parameters based on the information in the output signals generated by activity sensors 12, physiological sensors 14, and/or other sensors. In some embodiments, the parameters may be determined based on an analysis of the information in the output signals. The one or more physiological parameters, activity parameters, and/or other parameters determined by sensor information component 20 include a pulse/heart rate of subject 8; a blood pressure of subject 8; blood chemistry of subject 8; blood oxygen saturation of subject 8, hydration of subject 8; a respiration rate of subject 8; the cardiac output of subject 8, the skin/body temperature of subject 8, the relative health and/or sickness of subject 8; brain activity of subject 8; physical movement and/or lack of movement (e.g., during sleep) parameters; parameters related to performance and/or non-performance of daily activities by subject 8; activity duration parameters; parameters related to quantity and/or duration of interactions (social or otherwise) with other people; time duration between individual activities; an order of activities performed by subject 8; time spent in unfamiliar situations; an amount of time spent watching television, on the internet, or using computing devices; a type of information viewed while watching television, on the internet, or using computing devices; and/or other parameters. The information in the output signals from sensors 12 and/or 14, the parameters determined by sensor information component 20, and/or other information may be inputs for the electronic lucidity model (described below) and/or may be used for other purposes.

By way of several non-limiting examples, sensor information component 20 may be configured to determine a wake up time and/or sleep duration based on information from a bed sensor and/or smartphone accelerometer associated with subject 8. Sensor information component 20 may determine a number of snooze button presses based on information from sensors in an instrumented alarm clock and/or smartphone. Sensor information component 20 may determine parameters related to performance and/or non-performance of activities of daily living (grooming, eating breakfast, taking meds, watching television, etc.) based on information from sensors in rooms in the house of subject 8 (e.g., cameras, motion sensors, and/or other sensors); instrumented devices such as a coffeemaker, pillbox, and/or smart television; GPS location information as subject 8 moves around the house from a GPS sensor in a smartphone associated with subject 8; and/or other sensors. Sensor information component 20 may determine an order of activities of daily living, and/or time spent on and/or between the activities of daily living based on an analysis of the information described above. Sensor information component 20 may be configured to determine a physical activity level of subject 8 over a given time based on information from a wearable physical activity tracker and/or from sensors embedded in the smartphone associated with subject 8. Sensor information component 20 may be configured to determine an amount and/or duration of social interactions over a given time based on information from smartphone audio sensors, Bluetooth enabled devices, and/or other devices. Sensor information component 20 may be configured to determine an amount of time subject 8 spends in a less familiar environment (e.g., which would require a higher than normal demand on cognitive functioning) based on information from a smartphone GPS sensor. These examples should not be considered limiting. Sensor information component 20 is configured to determine any parameter that allows system 10 to function as described herein.

User input component 22 facilitates entry and/or selection of information by subject 8, caregivers, and/or other users. User input component 22 facilitates entry and/or selection of information via user interface 16 and/or other interface devices. For example, user input component 22 may cause user interface 16 to display one or more views of a graphical user interface to a caregiver which facilitate entry and/or selection of information by the caregiver. In some embodiments, user input component 22 is configured to facilitate entry and/or selection of information via one or more user interfaces 16 associated with one or more caregivers. In some embodiments, user input component 22 is be configured to facilitate entry and/or selection of information through a website, a mobile app, a bot through which text messages and/or emails are sent, and/or via other methods. In some embodiments, the entered and/or selected information includes information related to a mood of subject 8, information related to a cognitive state of subject 8, and/or other information. In some embodiments, user input component 22 is configured to prompt subject 8, caregivers, and/or other users to answer specific questions, provide ratings and/or levels of lucidity, and/or provide other information. In some embodiments, user input component 22 is configured to associate a time of day, a duration of time, and/or other time information with the entered and/or selected mood and/or cognitive state information. In some embodiments, user input component 22 facilitates entry and/or selection of a rating as well as the time period (e.g., the day so far, the past hour, the past week, etc.) for which this rating applies. The rating may be a binary rating for "lucid" or "not lucid", a three-level rating "low", "medium", "high", a rating between 1 to 10, and/or other ratings. User input component 22 is configured such that the mood and/or cognitive state information, the timing information, and/or other information may be inputs for the electronic lucidity model (described below), may be used to adjust the electronic lucidity model, and/or may be used for other purposes.

Model generation component 24 is configured to generate an electronic lucidity model for subject 8. Model generation component 24 is configured to generate the electronic lucidity model based on information previously received from sensors 12, sensors 14, sensor information component 20, user input component 22, and/or other information. In some embodiments, model generation component 24 is configured to generate the electronic lucidity model based on information determined from the information previously received from sensors 12, sensors 14, sensor information component 20, user input component 22, and/or other information.

In some embodiments, model generation component 24 is configured to generate the electronic lucidity model based on previous physical activity information (e.g., physical activity parameters), previous physiological parameter information (e.g., physiological parameters), previous mood information (e.g., ratings, etc.), previous cognitive state information (e.g., ratings, etc.), and/or other information. Previous physical activity information, previous physiological parameter information, previous mood information, and/or previous cognitive state information may be and/or include information generated, received, and/or determined by one or more components of system 10 before the electronic lucidity model for subject 8 is generated by model generation component. This information may be thought of as the information presently available for model generation component 24 to use to generate the electronic lucidity model. It should be noted that the previously mentioned types of information include any associated timing information and are not intended to be limiting.

In some embodiments, model generation component 24 is configured such that the electronic lucidity model is generated via machine learning and/or other techniques. Model generation component 24 is configured to substantially balance complexity, performance, and representation in the machine learning algorithm used to generate the electronic model. In some embodiments, model generation component 24 is configured such that the electronic lucidity model is generated via a multiple linear regression classifier. The previous physical activity information, previous physiological parameter information, previous mood information, and previous cognitive state information may be inputs to the multiple linear regression classifier and the current and/or predicted lucidity levels may be outputs, for example. In some embodiments, model generation component 24 is configured such that individual features (inputs) of the multiple linear regression classifier (or a logistic regression model in the case of two outputs for example) are first normalized to the same standard scale and then coefficients are derived for individual features based on the already labelled data (the previous physical activity information, previous physiological parameter information, previous mood information, and previous cognitive state information with their associated timing information). In some embodiments, model generation component 24 is configured such that the electronic lucidity model is generated via an artificial neural network. The previous physical activity information, previous physiological parameter information, previous mood information, and previous cognitive state information may be inputs to the first layer of the artificial neural network and the current and/or predicted lucidity level may be the output from the final layer of the artificial neural network, for example. One, two, or more hidden layers in the artificial neural network will allow for the system to find unique combinations of features that map to different lucidity levels. The output layer will include one node in which the lucidity level will be calculated/predicted from the model and input values. This approach allows for the model to reflect an individual user's unique situation and triggers for high or low lucidity.

As described below related to adjustment component 30, when additional information (physical activity parameters, physiological parameters, mood ratings, cognitive state ratings, associated timing information) is received, the electronic lucidity model is retrained based on the newly received information to further refine accuracy of current lucidity level indications and/or future lucidity level predictions output by the model.

Prediction component 26 is configured to determine a current lucidity level and/or predict the lucidity level of subject 8. Prediction component 26 is configured to determine the currently lucidity level and/or predict the lucidity level of subject 8 based on the electronic lucidity model and one or more of current physical activity information, current physiological parameter information, current mood information, current cognitive state information, and/or other information. Current physical activity information, current physiological parameter information, current mood information, and/or current cognitive state information may be and/or include information generated, received, and/or determined by one or more components of system 10 since (a current version of) the electronic lucidity model was generated by model generation component 24 and/or other information. For example, prediction component 26 is configured to substitute (e.g., replace the inputs of the model from when it was being trained/created with the actual inputs from the current situation for which a prediction is desired) current physical activity information, current physiological parameter information, current mood information, current cognitive state information, and/or other information into the electronic lucidity model generated by model generation component 24 and determine a current and/or predicted level for subject 8. In some embodiments, prediction component 26 is configured to determine a current lucidity level and/or predict the lucidity level of subject 8 in an ongoing manner, at predetermined intervals, response to a request by subject 8, a caregiver, and/or other users, responsive to the generation, reception, and/or determination of current information, and/or at other times.

In some embodiments, determining a current lucidity level and/or predicting the lucidity level of subject 8 comprises generating a current and/or predicted lucidity level score. In some embodiments, the score generated by prediction component is a score between 1 and 10, where 10 corresponds to high lucidity (relative to an individual's baseline) and 1 corresponds to low lucidity. In some embodiments, the score generated by prediction component 26 is a textual indication of lucidity. For example, the score generated by prediction component 26 may indicate whether subject 8 is having (or will have) a "good day" (high lucidity) or a "bad day" (low lucidity). These examples are not intended to be limiting. A lucidity level score generated by prediction component 26 may have any format that allows system 10 to function as described herein.

Communication component 28 is configured to communicate the current and/or predicted lucidity level of subject 8 to a caregiver of subject 8 and/or other people. In some embodiments, the communication includes an explanation of which current physical activity information, current physiological parameter information, current mood information, current cognitive state information and/or other information influenced the predicted lucidity level. Communication component 28 is configured to communicate via user interface 16, via email, via text messages, via a website, via a phone call, and or with other forms of communication. For example, in some embodiments, communication component 28 causes user interface 16 to display the lucidity level, the explanation, and/or other information to the caregiver, subject 8, and/or other people. In some embodiments, communication component 28 is configured to send an email or a text with such information to the caregiver, subject 8, and/or other people.

By way of a non-limiting example, communication component 28 may cause user interface 16 to display information to a caregiver that indicates that subject 8 will have a lucidity level of "6" tomorrow because today he had a moderate amount of physical activity (which would predict a good lucidity level) and is going to bed at the correct time of day, but had a socially demanding day because he had multiple visitors which caused commotion (which would predict poor lucidity the next day). As another example, communication component 28 may cause user interface 16 to display information to a caregiver that indicates a current lucidity level of subject 8 based on the activities of subject 8 during the day so far. Communication component 28 may send a text message at noon to a caregiver informing the caregiver of the current lucidity level of subject 8 as determined based on his morning routine. The text message may display a rating such as "medium" lucidity and indicate the predictive factor(s) ("late wake up time", "long dwell time for bathroom activity", "late blood sugar measurement", "low blood sugar level after eating") that caused the "medium" rating. In this way, caregivers may gain a better understanding of both the predicted lucidity level and also factors that system 10 has identified as potential influences on the lucidity level. The caregiver may then determine whether or not to follow up with subject 8 (e.g., in person, on the phone, etc.), arrange additional support for the individual, and/or take other actions.

Adjustment component 30 is configured to adjust the electronic lucidity model. Adjustment component 30 is configured to adjust the electronic lucidity model based on the current and/or predicted lucidity level and a cognitive state of subject 8 during a period of time that corresponds to the current and/or predicted lucidity level, and/or based on other information. Adjusting the electronic lucidity model may include adjusting which parameters/features are used as inputs, adjusting a relative importance of input parameters/features (e.g., adjusting coefficients in the algorithm), adjusting mathematical operations in the model, and/or other adjustments. To retrain the model over time based on new ratings of lucidity by the user, caregiver, or any other observer, a batch-incremental and/or instance-incremental ("online") approach, and/or other approaches may be used. With the batch-incremental approach, this new lucidity rating is associated with the current and recent history of the user's context, and is added to the existing data set. Substantially the entire data set (and/or subsets of the dataset) may be used to retrain the neural network, for example. In the instance-incremental approach, the new lucidity rating and/or the associated context is used as a training instance and the weights are adjusted based on the difference between the model's predicted output and the actual lucidity rating.

When additional information (physical activity parameters, physiological parameters, mood ratings, cognitive state ratings, associated timing information) is received, the electronic lucidity model is retrained based on the newly received information and/or other information to further refine accuracy of current lucidity level indications and/or future lucidity level predictions output by the model. In some embodiments, adjustment component 30 is configured to adjust the electronic lucidity model based on individual predicted/actual lucidity level observations (e.g., does a predicted lucidity level match an actual lucidity level observation). In some embodiments, adjustment component 30 is configured to adjust the electronic lucidity model based on multiple predicted/actual lucidity level observations (e.g. do the predicted lucidity levels generally match the observed lucidity levels). In some embodiments, adjustment component 30 is configured to learn (e.g., via a regression classifier analysis and/or other analysis techniques) what information, parameters, and/or other factors are most predictive of lucidity/confusion. Adjustment component 30 is configured to give such information, parameters, and/or other factors greater weight in the electronic lucidity model relative to other information, parameters, and/or other factors.

For example, prediction component 26 may predict a lucid next day for subject 8 wherein a strong predictive parameter was normal performance of a daily routine the day before. In actuality, it may turn out that subject 8 has a confused and non-lucid day instead. A caregiver may enter and/or select information via user interface 16 (facilitated by user input component 22) that indicates the non-lucid next day to system 10. Adjustment component 30 may compare the information received from the caregiver to the predicted lucidity level from prediction component 26 and adjust the electronic lucidity model based on the comparison (e.g., by giving the daily routine parameter less weight to predict lucidity and/or more weight in predicting confusion). In this example, adjustment component 30 may adjust the electronic lucidity model such that one or more of the parameter inputs/feature values, coefficients, etc., in the machine learning algorithm that were influential in predicting the lucid day are adjusted so that the model would have predicted the actual (non) lucidity based on the same information.

Electronic storage 40 comprises electronic storage media that electronically stores information. The electronic storage media of electronic storage 40 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 40 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 40 may store software algorithms, information determined by processor 18, information received via user interface 16 and/or external computing systems, information received from activity sensors 12 and/or physiological sensors 14, and/or other information that enables system 10 to function as described herein. Electronic storage 40 may be (in whole or in part) a separate component within system 10, or electronic storage 40 may be provided (in whole or in part) integrally with one or more other components of system 10 (e.g., user interface 16, processor 20).

Figure 2:
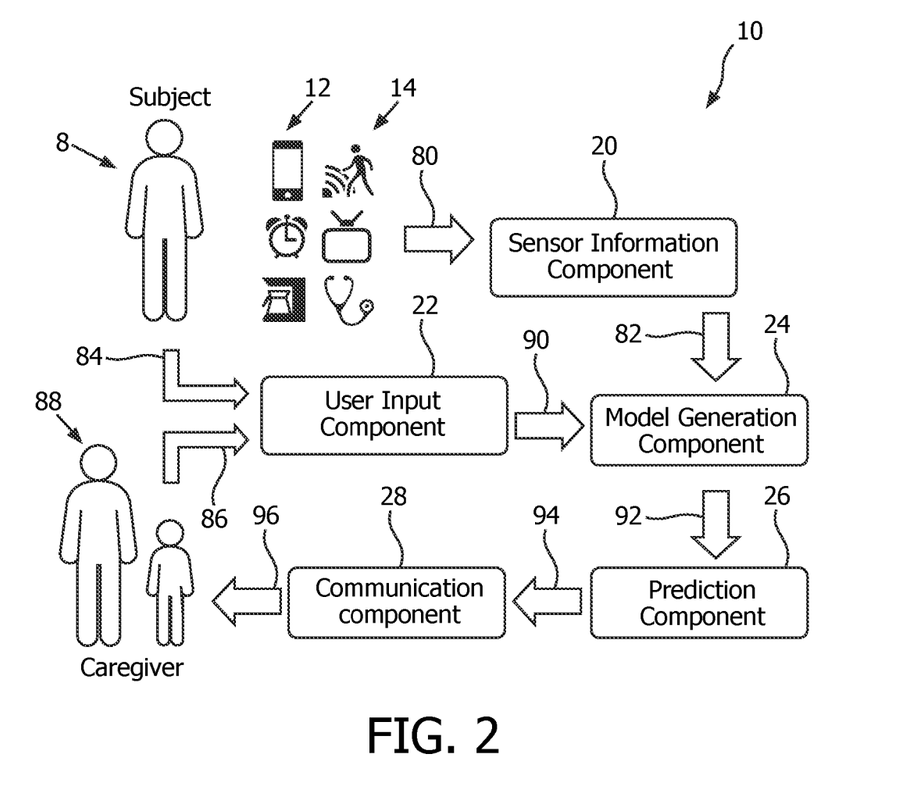
FIG. 2 illustrates operation of the system.

FIG. 2 illustrates operation of system 10. Sensors 12, 14, and/or other sensors generate output signals that convey information 80 related to the physical activity of subject 8, the physiological parameters of subject 8, and/or other information. Sensor information component 20 receives the information from the sensors and determines one or more activity parameters, physiological parameters, and/or other parameters based on the information in the output signals generated by activity sensors 12, physiological sensors 14, and/or other sensors. Sensor information component 20 communicates 82 the determined information, the information conveyed by the sensor output signals, and/or other information to model generation component 24. User input component 22 facilitates entry and/or selection of information 84 by subject 8, information 86 by caregivers 88, and/or other users. User input component 22 communicates 90 the received and/or selected information and/or other information to model generation component 24. The electronic lucidity model for subject 8 is generated by model generation component 24 based on the information and/or parameters received from sensor information component 20, the information from user input component 22 and/or other information. Model generation component 24 communicates 92 the generated electronic model to prediction component 26, which substitutes current information (e.g., information conveyed in the sensor output signals, parameters determined by sensor information component 20, information received from user input component 22, etc.) for subject 8 into the model and outputs 94 an indication of the lucidity level of subject 8 and/or predicts a future lucidity level of subject 8. Communication component 28 communicates 96 the current and/or predicted lucidity level of subject 8 to caregiver 88 of subject 8 and/or other people. Adjustment component 30 (not shown in FIG. 2) is configured to adjust the electronic lucidity model based on the current and/or predicted lucidity level and a cognitive state of subject 8 during a period of time that corresponds to the current and/or predicted lucidity level (e.g., as entered and/or selected by caregiver 88 and received 86 by user input component 22), and/or based on other information.

As shown in FIG. 2 (and described herein), system 10 receives and/or generates highly dimensional data and aggregates the information over time. The lives of subject 8 and/or caregiver 88 may be very "noisy" which makes pinpointing (by subject 8, caregiver 88, and/or human beings) events and/or other aspects of the dimensional data before and/or after episodes of lucidity and/or confusion by subject 8 difficult. System 10 determines correlations over time between the dimensional data and the episodes of confusion/lucidity (e.g., system 10 generates the electronic lucidity model and adjusts it over time as new information is received/determined). System 10 determines correlations that are not able to be determined by humans without the help of an electronic system such as system 10. For example, a parameter of subject 8 that drifts slowly over time (e.g., very small changes in a daily routine) may not be noticeable to a normal human caregiver because the caregiver may not spend all day every day with subject 8, the caregiver may be distracted by other things, etc. System 10 may detect subtle changes in timing, an order of events and/or other changes. This small drift may influence lucidity/confusion of subject 8. Without system 10, this drift would never be identified and subject 8 may go on experiencing days of non-lucidity because the daily routine of subject 8 continues to drift over time.

Figure 3:
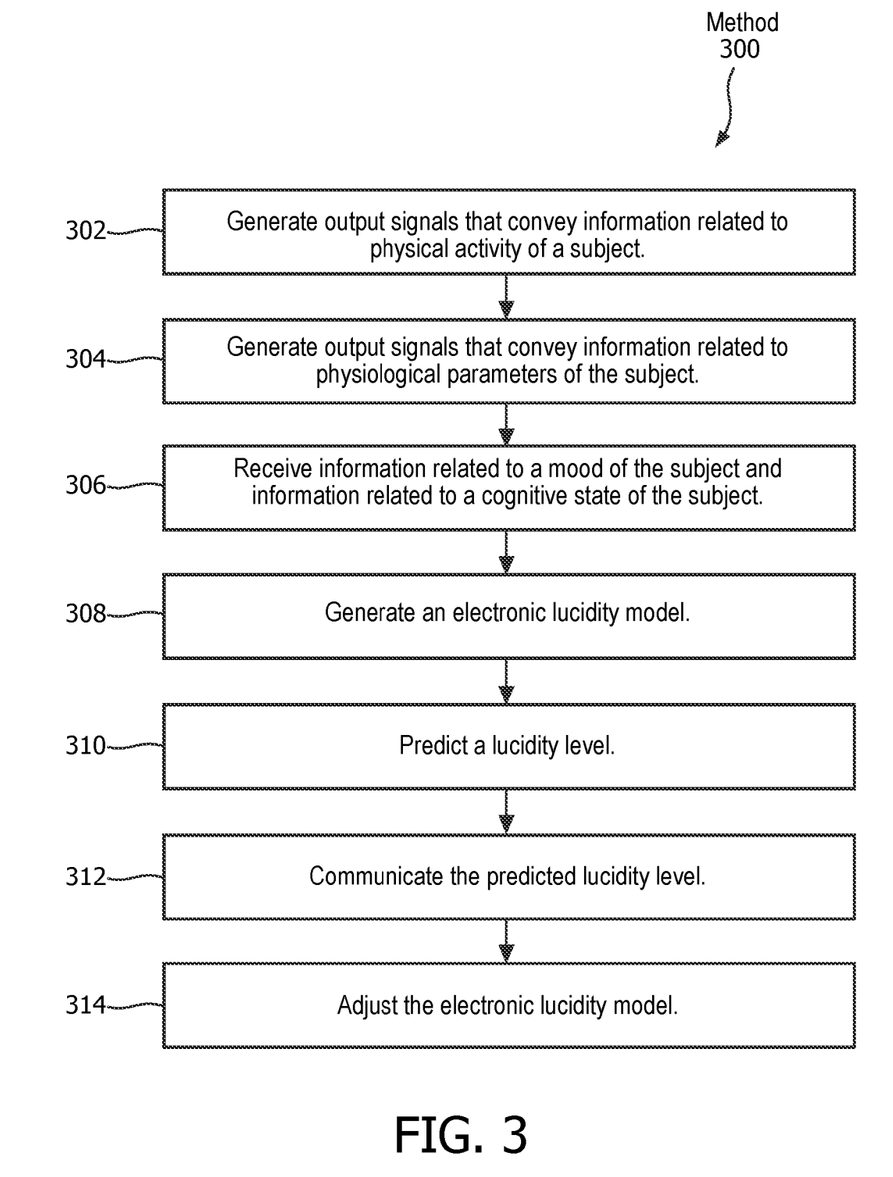
FIG. 3 illustrates a method for predicting a lucidity level of a subject with a prediction system.

FIG. 3 illustrates a method 300 for predicting a lucidity level of a subject with a prediction system. The system comprises one or more one or more activity sensors, one or more physiological sensors, a user interface, one or more hardware processors, and/or other components. The one or more physical computer processors are configured to execute computer program components. The computer program components comprise a sensor information component, a user input component, a model generation component, a prediction component, a communication component, an adjustment component, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, output signals conveying information related to physical activity of a subject are generated. The output signals are generated by one or more activity sensors and/or other devices. In some embodiments, the one or more activity sensors include one or more of a motion sensor, a geolocation sensor, a sleep sensor, a clock, instrumented household appliances, a camera, a wearable activity tracker, a smartphone, and/or other sensors. In some embodiments, operation 302 is performed by one or more sensors the same as or similar to activity sensors 12 (shown in FIG. 1 and described herein).

At an operation 304, output signals that convey information related to physiological parameters of the subject are generated. The output signals are generated by one or more physiological sensors and/or other devices. In some embodiments, the one or more physiological sensors include one or more of a heart rate monitor, a blood pressure monitor, a blood glucose monitor, a hydration monitor, and/or other sensors. In some embodiments, operation 304 is performed by one or more sensors the same as or similar to physiological sensors 14 (shown in FIG. 1 and described herein).

At an operation 306, information related to a mood of the subject and information related to a cognitive state of the subject is received. In some embodiments, operation 306 is performed by a user interface the same as or similar to user interface 16 (shown in FIG. 1 and described herein).

At an operation 308, an electronic lucidity model is generated. In some embodiments, the electronic lucidity model is generated based on previous physical activity information, previous physiological parameter information, previous mood information, previous cognitive state information, and/or other information. In some embodiments, the electronic lucidity model is generated via a multiple linear regression classifier where the previous physical activity information, previous physiological parameter information, previous mood information, and previous cognitive state information are inputs to the multiple linear regression classifier and the predicted lucidity level is an output. In some embodiments, operation 308 is performed by a processor component the same as or similar to model generation component 24 (shown in FIG. 1 and described herein).

At an operation 310, a lucidity level is predicted. In some embodiments, the lucidity level is predicted based on the electronic lucidity model and one or more of current physical activity information, current physiological parameter information, current mood information, current cognitive state information, and/or other information. In some embodiments, predicting the lucidity level comprises generating a predicted lucidity level score. In some embodiments, operation 310 is performed by a processor component the same as or similar to prediction component 26 (shown in FIG. 1 and described herein).

At an operation 312, the predicted lucidity level is communicated. In some embodiments, the predicted lucidity level is communicated to a caregiver of the subject and/or other users. In some embodiments, the communication includes an explanation of which current physical activity information, current physiological parameter information, current mood information, and/or current cognitive state information influenced the predicted lucidity level. In some embodiments, operation 312 is performed by a processor component the same as or similar to communication component 28 (shown in FIG. 1 and described herein).

At an operation 314, the electronic lucidity model is adjusted. The electronic lucidity model is adjusted based on the predicted lucidity level and a future cognitive state of the subject during a period of time that corresponds to the predicted lucidity level, and/or other information. In some embodiments, operation 314 is performed by a processor component the same as or similar to adjustment component 30 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to predict a lucidity level of a subject, the system comprising:
    one or more activity sensors configured to generate output signals conveying information related to physical activity of the subject;
    one or more physiological sensors configured to generate output signals conveying information related to physiological parameters of the subject;
    a user interface configured to receive information related to a mood of the subject and information related to a cognitive state of the subject; and
    one or more hardware processors configured by machine-readable instructions to:
        generate an electronic lucidity model for the subject based on previous physical activity information, previous physiological parameter information, previous mood information, and previous cognitive state information; and
        predict the lucidity level of the subject based on the electronic lucidity model and one or more of current physical activity information, current physiological parameter information, current mood information, or current cognitive state information.

2. The system of claim 1, wherein the one or more hardware processors are further configured by machine-readable instructions to communicate the predicted lucidity level to a caregiver of the subject, the communication including an explanation of which of the current physical activity information, the current physiological parameter information, the current mood information, and/or the current cognitive state information influenced the predicted lucidity level.

3. The system of claim 1, wherein the one or more hardware processors are further configured by machine-readable instructions to adjust the electronic lucidity model based on the predicted lucidity level and a future cognitive state of the subject during a period of time that corresponds to the predicted lucidity level.

4. The system of claim 1, wherein the one or more hardware processors are further configured by machine-readable instructions such that the electronic lucidity model is generated via a multiple linear regression classifier where the previous physical activity information, the previous physiological parameter information, the previous mood information, and the previous cognitive state information are inputs to the multiple linear regression classifier and the predicted lucidity level is an output.

5. The system of claim 1, wherein the one or more hardware processors are further configured by machine-readable instructions such that predicting the lucidity level comprises generating a predicted lucidity level score.

6. The system of claim 1, wherein:
    the one or more activity sensors include one or more of a motion sensor, a geolocation sensor, a sleep sensor, a clock, instrumented household appliances, a camera, a wearable activity tracker, or a smartphone; and
    the one or more physiological sensors include one or more of a heart rate monitor, a blood pressure monitor, a blood glucose monitor, or a hydration monitor.

7. A method for predicting a lucidity level of a subject with a prediction system, the prediction system comprising one or more activity sensors, one or more physiological sensors, a user interface, and one or more hardware processors, the method comprising:
    generating, with the one or more activity sensors, output signals conveying information related to physical activity of the subject;
    generating, with the one or more physiological sensors, output signals conveying information related to physiological parameters of the subject;
    receiving, with the user interface, information related to a mood of the subject and information related to a cognitive state of the subject;
    generating, with the one or more hardware processors, an electronic lucidity model for the subject based on previous physical activity information, previous physiological parameter information, previous mood information, and previous cognitive state information; and
    predicting, with the one or more hardware processors, the lucidity level of the subject based on the electronic lucidity model and one or more of current physical activity information, current physiological parameter information, current mood information, or current cognitive state information.

8. The method of claim 7, further comprising:
    communicating, with the one or more hardware processors, the predicted lucidity level to a caregiver of the subject, the communication including an explanation of which of the current physical activity information, the current physiological parameter information, the current mood information, and/or the current cognitive state information influenced the predicted lucidity level.

9. The method of claim 7, further comprising:
adjusting, with the one or more hardware processors, the electronic lucidity model based on the predicted lucidity level and a future cognitive state of the subject during a period of time that corresponds to the predicted lucidity level.

10. The method of claim 7, further comprising:
generating the electronic lucidity model via a multiple linear regression classifier where the previous physical activity information, the previous physiological parameter information, the previous mood information, and the previous cognitive state information are inputs to the multiple linear regression classifier and the predicted lucidity level is an output.

11. The method of claim 7, wherein predicting the lucidity level further comprises:
generating a predicted lucidity level score.

12. The method of claim 7, wherein:
the one or more activity sensors include one or more of a motion sensor, a geolocation sensor, a sleep sensor, a clock, instrumented household appliances, a camera, a wearable activity tracker, or a smartphone; and
the one or more physiological sensors include one or more of a heart rate monitor, a blood pressure monitor, a blood glucose monitor, or a hydration monitor.

13. A system configured to predict a lucidity level of a subject, the system comprising:
means for generating output signals conveying information related to physical activity of the subject;
means for generating output signals conveying information related to physiological parameters of the subject;
means for receiving information related to a mood of the subject and information related to a cognitive state of the subject;
means for generating an electronic lucidity model for the subject based on previous physical activity information, previous physiological parameter information, previous mood information, and previous cognitive state information; and
means for predicting the lucidity level of the subject based on the electronic lucidity model and one or more of current physical activity information, current physiological parameter information, current mood information, or current cognitive state information.

14. The system of claim 13, further comprising:
means for communicating the predicted lucidity level to a caregiver of the subject, the communication including an explanation of which of the current physical activity information, the current physiological parameter information, the current mood information, and/or the current cognitive state information influenced the predicted lucidity level.

15. The system of claim 13, further comprising:
means for adjusting the electronic lucidity model based on the predicted lucidity level and a future cognitive state of the subject during a period of time that corresponds to the predicted lucidity level.

16. The system of claim 13, wherein the means for generating the electronic lucidity model are further configured such that the electronic lucidity model is generated via a multiple linear regression classifier where the previous physical activity information, the previous physiological parameter information, the previous mood information, and the previous cognitive state information are inputs to the multiple linear regression classifier and the predicted lucidity level is an output.

17. The system of claim 13, wherein the means for predicting the lucidity level are further configured such that predicting the lucidity level comprises generating a predicted lucidity level score.

18. The system of claim 13, wherein:
the means for generating output signals conveying information related to physical activity of the subject include one or more of a motion sensor, a geolocation sensor, a sleep sensor, a clock, instrumented household appliances, a camera, a wearable activity tracker, or a smartphone; and
the means for generating output signals conveying information related to physiological parameters of the subject include one or more of a heart rate monitor, a blood pressure monitor, a blood glucose monitor, or a hydration monitor.

* * * * *